United States Patent [19]
Nobles

[11] Patent Number: 5,766,195
[45] Date of Patent: Jun. 16, 1998

[54] OPTICAL SHUNT CUTTER SYSTEM

[75] Inventor: Anthony A. Nobles, Fountain Valley, Calif.

[73] Assignee: Cordis Innovasive Systems, Inc., Miami Lakes, Fla.

[21] Appl. No.: 215,130

[22] Filed: Mar. 18, 1994

[51] Int. Cl.$^6$ .................................................. A61B 17/32
[52] U.S. Cl. ........................... 606/170; 606/159; 606/167
[58] Field of Search .......................... 606/27, 38, 159, 606/170, 171, 180, 167; 604/22

[56] References Cited

U.S. PATENT DOCUMENTS

| | | |
|---|---|---|
| 2,521,161 | 9/1950 | Grover . |
| 2,729,210 | 1/1956 | Spencer . |
| 2,730,101 | 1/1956 | Hoffman . |
| 3,605,721 | 9/1971 | Hallac . |
| 3,815,604 | 6/1974 | O'Malley et al. . |
| 4,428,748 | 1/1984 | Peyman et al. . |
| 4,441,509 | 4/1984 | Kotsifas et al. . |
| 4,598,710 | 7/1986 | Kleinberg et al. . |
| 4,640,296 | 2/1987 | Schnepp-Pesch et al. . |
| 4,646,738 | 3/1987 | Trott . |
| 4,689,040 | 8/1987 | Thompson . |
| 4,705,038 | 11/1987 | Sjostrom et al. . |
| 4,708,147 | 11/1987 | Haaga . |
| 4,732,154 | 3/1988 | Shiber . |
| 4,757,826 | 7/1988 | Abdulhay . |
| 4,887,613 | 12/1989 | Farr et al. . |
| 5,077,506 | 12/1991 | Krause . |
| 5,092,872 | 3/1992 | Segalowitz ............................. 606/159 |
| 5,242,461 | 9/1993 | Kortenbach et al. ................... 606/159 |
| 5,282,484 | 2/1994 | Reger ..................................... 606/159 |
| 5,318,576 | 6/1994 | Plassche, Jr. et al. .................. 606/159 |

*Primary Examiner*—William Lewis
*Attorney, Agent, or Firm*—Jeffrey P. Wall

[57] ABSTRACT

A device and method for removing ingrown biological tissue from the fluid passageway of a drainage shunt which has been implanted in a patient to relieve a hydrocephalic condition, includes a tubular catheter which is slidably insertable through the passageway of the drainage shunt. A blade extends from the distal end of the catheter and, as the tubular catheter is rotated, the blade cuts away any biological tissue which has ingrown in the passageway. A viewing element is insertable through the tubular catheter to view the blade's progress through the tubular catheter and determine its relationship with any tissue that has ingrown in the passageway.

3 Claims, 2 Drawing Sheets

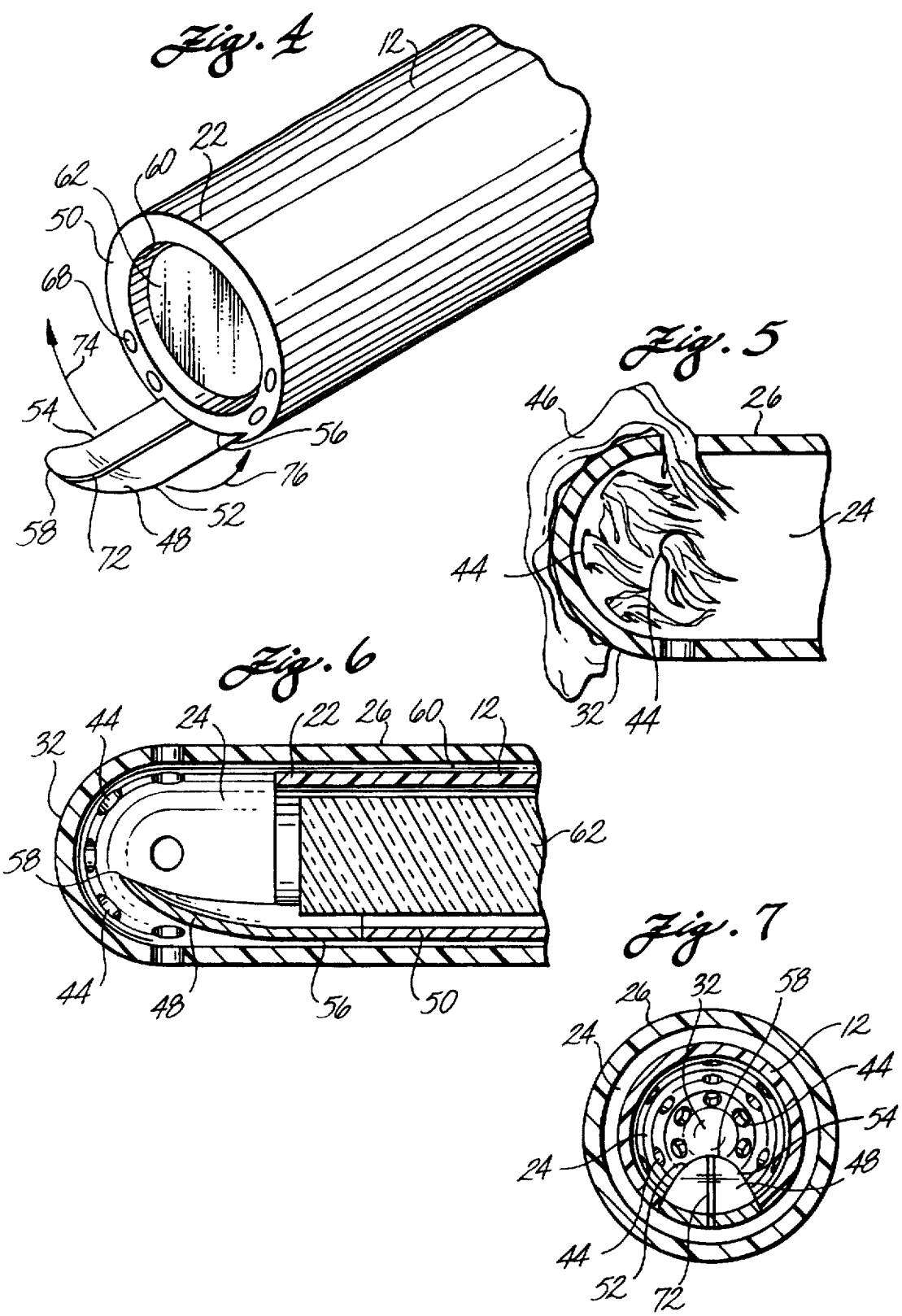

OPTICAL SHUNT CUTTER SYSTEM

FIELD OF THE INVENTION

The present invention pertains generally to medical devices. More specifically, the present invention pertains to medical devices which can restore the operational capability of other devices or apparatus that have been previously implanted in a patient, and can do so without requiring removal of the implanted device or apparatus from the patient. The present invention is particularly, but not exclusively, useful as a device for removing ingrown biological tissue from the fluid passageway of a drainage shunt which has been implanted in a patient to relieve a hydrocephalic condition.

BACKGROUND OF THE INVENTION

Hydrocephalus, sometimes loosely referred to as "water on the brain", is a condition which is marked by obstruction of the cerebrospinal fluid pathways and is accompanied by an accumulation of cerebrospinal fluid within the skull. Usually the cerebrospinal fluid is under increased pressure and several complications can result. The most debilitating of these complications are brain atrophy, mental deterioration and convulsions. Obviously, hydrocephalus is a condition which requires treatment.

A commonly used device for the treatment of hydrocephalus is a drainage shunt which relieves fluid pressure in the skull. This is accomplished by providing a passageway through which cerebrospinal fluid can be evacuated from the affected area of the brain. To do this, the exact placement of the drainage shunt in the skull is an extremely important consideration. Specifically, the distal end of the shunt needs to be placed where it can most effectively collect and evacuate cerebrospinal fluid before it accumulates. More specifically, this means the distal end of the drainage shunt should be placed in near proximity to the choroid plexus, since it is the choroid plexus which secretes the cerebrospinal fluid. Unfortunately, the choroid plexus includes enfoldings of blood vessels which form tufted projections that can entangle and clog the fluid ports of the drainage shunt.

Whenever the choroid plexus clogs the fluid ports of the drainage shunt, the shunt becomes ineffective for its intended purpose. In the past, in order to restore proper drainage of cerebrospinal fluid from the skull, it has been necessary to replace the shunt. This has required extrication of the shunt from the choroid plexus for removal of the shunt from the patient and its subsequent replacement.

The present invention recognizes that a clogged drainage shunt need not necessarily be replaced. Instead, as recognized by the present invention, choroid plexus tissue which has grown into the passageway of the drainage shunt, or which has otherwise clogged the ports of the shunt, can be cut and removed from inside the passageway of the shunt. Thus, the shunt need not necessarily be removed from the patient and replaced by another shunt in order to restore its patency for proper drainage of cerebrospinal fluid from the brain.

In light of the above it is an object of the present invention to provide a device for cutting ingrown tissue from the passageway of a drainage shunt which can restore the patency of the drainage shunt without unnecessarily removing the shunt from the patient. It is another object of the present invention to provide a device for cutting ingrown tissue from the passageway of a drainage shunt which allows the user to visually monitor the removal of such tissue from the passageway. Still another object of the present invention is to provide a device for cutting ingrown tissue from the passageway of a drainage shunt which is simple to use, relatively easy to manufacture and comparatively cost effective.

SUMMARY OF THE INVENTION

In accordance with the present invention, a device for removing ingrown tissue from the fluid passageway of a drainage shunt includes a tubular catheter which is insertable into the fluid passageway. The tubular catheter is formed with a lumen and has a blade which extends from its distal end. Also, the device includes a viewing element which is insertable through the lumen of the tubular catheter to view the progress and location of the blade as the blade is advanced through the passageway of the drainage shunt and into contact with the ingrown tissue.

The blade of the device of the present invention extends from the peripheral wall of the tubular catheter and is inclined inwardly from the catheter wall toward the central axis of the tubular catheter. Also, the blade is slightly curved, and is formed with opposed first and second cutting edges which will respectively cut tissue as the tubular catheter is rotated in either a clockwise or a counterclockwise direction. Further, the blade can be made of an electrically resistive material which will become heated whenever an electric current is applied. With a heated blade, the device is able to thermally cut or electro-cauterize the tissue that is in contact with the blade.

During an advancement of the tubular catheter into and through the passageway of the drainage shunt, the viewing device can be used to monitor the position and location of the blade relative to the ingrown tissue to be excised. For the present invention, this viewing element is preferably an optical fiber which can be inserted and advanced through the lumen of the tubular catheter to place the distal end of the optical fiber into a position where the distal end of the tubular catheter, and the blade attached thereto, can be observed. A connector at the proximal end of the optical fiber allows the user to optically attach an appropriate scope or viewing device to the proximal end of the optical fiber in order to visualize the use and effectiveness of the blade.

Preferably, the device of the present invention also includes an irrigation channel which can be formed as part of the tubular catheter. For the present invention the irrigation channel can either be formed into the wall of the catheter to extend substantially along the entire length of the tubular catheter, or the irrigation channel can be connected into direct fluid communication with the lumen of the tubular catheter at a proximal location. For either embodiment of the irrigation channel, its purpose is provide the user with the ability to irrigate the passageway of the drainage shunt to improve visibility in the passageway of the shunt or to assist in the removal of cut tissue debris from the passageway.

The novel features of this invention, as well as the invention itself, both as to its structure and its operation will be best understood from the accompanying drawings, taken in conjunction with the accompanying description, in which similar reference characters refer to similar parts, and in which:

BRIEF DESCRIPTION OF THE DRAWINGS

FIG. 4 is a perspective view of the distal tip end portion of the optical shunt cutter device of the present invention;

FIG. 5 is a cross-sectional view of the distal end portion of a drainage shunt with ingrown biological tissue in the passageway of the drainage shunt as would be seen along the line 6—6 in FIG. 3;

FIG. 6 is a cross-sectional view of the distal end portion of the device of the present invention when inserted into the passageway of a drainage shunt as would be seen along the line 6—6 in FIG. 3; and FIG. 7 is an end-on view of the passageway and distal end of a drainage shunt, and a cross-sectional view of the device of the present invention when inserted into the drainage shunt, as would be seen along the line 7—7 in FIG. 3.

BRIEF DESCRIPTION OF THE PREFERRED EMBODIMENTS

Figure 1:
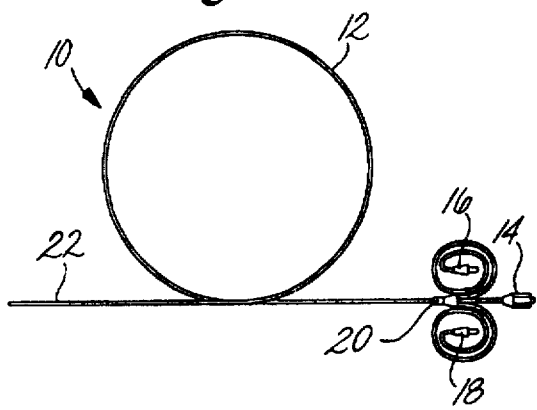
FIG. 1 is a plan view of the optical shunt cutter device of the present invention.

Referring initially to FIG. 1, the optical shunt cutter device of the present invention is shown and generally designated 10. As shown, the device 10 includes an elongated tubular catheter 12 having an optical connector 14, a fluid source connector 16, and a voltage source connector 18. The connectors 14, 16 and 18 are located substantially at the proximal end 20 of the tubular catheter 12 and are respectively connectable to system accessories. For purposes of the present invention, the tubular catheter 12 is made of a flexible material which will allow the distal end 22 of catheter 12 to be easily inserted into and advanced through the passageway 24 of a drainage shunt 26.

Figure 2:
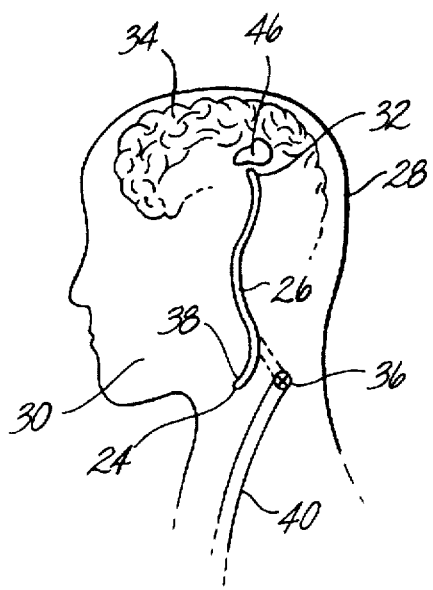
FIG. 2 is a schematic view of a drainage shunt positioned in the head of a patient to relieve a hydrocephalus condition.

Referring now to FIG. 2 it will be seen that for its intended operation, the drainage shunt 26 is positioned in the head 28 of a patient 30. Specifically shunt 26 is positioned with its distal end 32 positioned near the brain 34 of patient 30 to allow for drainage of cerebrospinal fluid, "water", from the area of the brain 34. Specifically, the positioning of shunt 26 as shown in FIG. 2 is intended to relieve a hydrocephalic condition. Further, it will be seen in FIG. 2 that the proximal end 38 of drainage shunt 26 has been disconnected from a valve 36 to allow for access into the passageway 24 of the drainage shunt 26. For normal operation of the drainage shunt 26, however, the proximal end 38 is connected to valve 36, as indicated by the dashed lines in FIG. 2, to establish fluid communication between shunt 26 and the fluid drain line 40. This connection allows for the transfer of water from the area of brain 34 to the chest area 42 of patient 30. The proper operation of the shunt 26, however, requires that the passageway 24 of shunt 26 remain patent.

As can be easily appreciated, the patency of passageway 24 is compromised whenever the ports 44 in distal end 32 of shunt 26 (see FIG. 5) become clogged or occluded. This condition can happen if the distal end 32 of shunt 26 is inadvertently placed too near the choroid plexus 46 of brain 34. Should this happen, it is possible the choroid plexus 46 will grow into passageway 24 through the ports 44 of shunt 26 and thereby disrupt the drainage of water from brain 34 through shunt 26. This condition is to be avoided and, if it should occur, proper drainage needs to be restored by using the device 10. Use of the device 10, however, requires that the shunt 26 be disconnected from valve 36.

Figure 3:
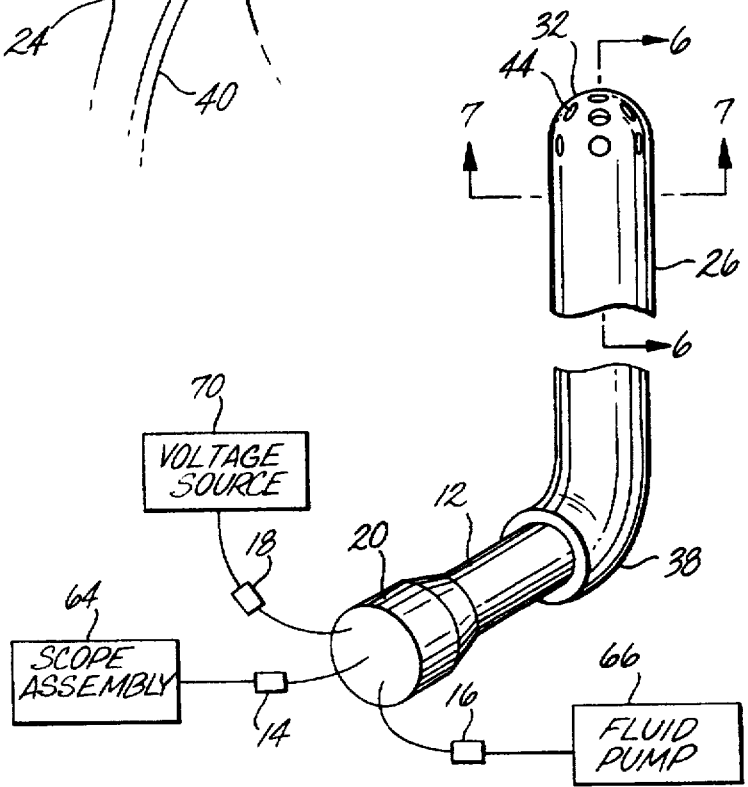
FIG. 3 is a perspective view of the device of the present invention engaged with a drainage shunt.

As perhaps best seen in FIG. 3, use of the device 10 requires that distal end 22 of tubular catheter 12 be inserted into the passageway 24 of shunt 26. Access into the passageway 24 is achieved through the proximal end 38 of shunt 26 after it has been disconnected from the valve 36.

After shunt 26 has been disconnected from valve 36, and the distal end 22 of tubular catheter 12 has been inserted into passageway 24, the tubular catheter 12 is advanced through the passageway 24 of shunt 26. Advancement of the catheter 12 continues until its distal end 22 is near the tissue of choroid plexus 46 which has become entangled with ports 44 and grown into passageway 24 of drainage shunt 26.

The structure of device 10 at the distal end 22 of tubular catheter 12 is best seen in FIG. 4. There it will be seen that a blade 48 extends distally from a portion of the wall 50 of tubular catheter 12. Further, FIG. 4 shows that the blade 48 has a first cutting edge 52 and a second cutting edge 54 on the opposite side of blade 48. The base 56 of blade 48 is securely anchored and attached to the wall 50 of tubular catheter 12 by any suitable means well known in the art, such as by bonding. This places the tip 58 of blade 48 at some distance in front of the distal end 22 of catheter 12. As shown in FIG. 4, and perhaps more fully appreciated by cross referencing FIG. 4 with FIGS. 6 and 7, the blade 48 is preferably inclined inwardly from the wall 50 of tubular catheter 12 toward the central longitudinal axis of the tubular catheter 12. Further, in addition to being so inclined, the blade 48 may be curved or rounded in its inclination. Preferably, blade 48 has the same curvature as the inside surface of the distal end 32 of drainage shunt 26. This similarity in curvature will allow the cutting edges 52 and 54 of blade 48 to pass over the ports 44 to achieve a more efficient cutting of the tissue.

Still referring to FIG. 4, it will be seen that tubular catheter 12 is formed with a lumen 60 which extends the entire length of the catheter 12. Through this lumen 60, and optical fiber 62 can be advanced until it is positioned, substantially as shown in FIG. 4 to assist in visually monitoring the location and operation of blade 48.

Returning to FIGS. 1 and 3, it is to be appreciated that several system accessories are useable with the device 10 of the present invention. For example, in FIG. 3 a scope assembly 64 is schematically shown attached to the optical connector 14 of device 10 to establish a viewing path from the scope assembly 64 through the optical fiber 62 and out the distal end 22 of tubular catheter 12. For purposes of the present invention, scope assembly 64 can either be a simple eyepiece or a more sophisticated electronic imaging device, depending on the desires of the user.

FIG. 3 also shows a fluid pump 66 attached to the fluid source connector 16 of device 10. As intended for the present invention, a fluid, such as a saline solution, is selectively pumped through the tubular catheter 12 to its distal end 22 in order to enhance visibility in the passageway 24 of shunt 26. In one embodiment of the device 10, the fluid source connector establishes fluid communication from the fluid pump 66 (and its fluid source) directly into the lumen 60 of tubular catheter 12. For this embodiment, the fluid is pumped through the lumen 60 and out of distal end 22 of catheter 12. In an alternate embodiment (suggested in FIG. 4) the wall 50 of tubular catheter 12 includes at least one channel 68. For this alternate embodiment, fluid connector 16 establishes fluid communication from the fluid pump 66 into the channel 68 and the fluid is pumped through the channel 68 to the distal end 22 of catheter 12.

As indicated above, it is an intention of the present invention that the blade 48 of device 10 be heatable in order to thermally cut or electro-coagulate tissue which has grown into the passageway 24 of shunt 26. Consequently, as shown in FIG. 3, device 10 provides for the attachment of a voltage source 70 to the voltage source connector 18. Through the connector 18, the voltage source is electrically connectable to the blade 48 by way of wires (not shown) which can be implanted into the wall 50 of catheter 12. Several electrical configurations for using electrical current from the voltage source 70 to heat blade 48 are possible and these configuration can be either monopole or bipole. For a bipole configuration, a dielectric strip 72 as shown in FIGS. 4 and 7 is necessary to electrically separate cutting edges 52 and 54 of the blade 48 from each other. In any configuration, the material which is used for blade 48 must be any well known electrically resistive material which will achieve the desired result.

OPERATION

In the operation of the device 10 for removing ingrown tissue from the fluid passageway 24 of drainage shunt 26, the shunt 26 is first disconnected from valve 36 and its proximal end 38 is extracorporeally exposed. The distal end 22 of tubular catheter 12 is then inserted into the passageway 24 of shunt 26, and blade 48 is advanced into contact with tissue from choroid plexus 46 which may have grown through the ports 44 and into the passageway 24 of shunt 26. As the tubular catheter 12 is being advanced through passageway 24, the user can visually monitor the procedure by using the scope assembly 64 to view blade 48 of device 10 and the distal end 32 of drainage shunt 26 as generally shown in FIG. 7.

With blade 48 positioned near distal end 32 of drainage shunt 26 as shown in FIG. 6, the device 10 can be rotated, in the directions indicated by arrows 74 and 76 in FIG. 4, to cut ingrown tissue from the passageway 24. Thus, the catheter 12 can be rotated either clockwise or counterclockwise to cause the respective cutting edges 52 or 54 of blade 48 to cut tissue from the passageway 24. While neither FIG. 6 nor FIG. 7 show ingrown tissue, it is to be appreciated that before the cutting operation with device 10 has been completed, tissue as shown in FIG. 5 will be present. This tissue has been omitted from FIGS. 6 and 7 for purposes of clarity.

According to the desires of the user, the blade 48 can be selectively heated to thermally cut or electro-cauterize tissue in the passageway 24. This is accomplish by activation of the voltage source 70. Also, activation of the fluid pump 66 by the user will selectively introduce fluid through the lumen 60 of catheter 12 to use the lumen 60 as irrigation channel for irrigating the passageway 24 to improve visibility in the passageway 24 during use of the device 10.

While the particular device and method for removing ingrown tissue from the fluid passageway of a drainage shunt as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

I claim:

1. A device for removing ingrown tissue from the fluid passageway of a drainage shunt which comprises:

a tubular catheter formed with a lumen and having a proximal end and a distal end, said catheter being slidably insertable through said passageway of said drainage shunt;

a blade attached to said catheter and extending from said distal end thereof, said blade being rotatable with said tubular catheter in said passageway for cutting ingrown tissue in said passageway; and a means for selectively heating said blade to electrocauterize tissue in said passageway.

2. A device for removing ingrown tissue from the fluid passageway of a drainage shunt which comprises:

a tubular catheter formed with a lumen and having a proximal end and a distal end, wherein said catheter is slidably insertable through said passageway of said drainage shunt, said catheter is characterized by a longitudinally oriented central axis, and said catheter is rotatable in said passageway of said shunt; and a blade attached to said catheter and extending from said distal end thereof for cutting ingrown tissue in said passageway, wherein said blade is curved and has a base and a tip, said tip being attached to said catheter and said tip being inclined toward the central axis of said catheter, and wherein said blade has a first cutting edge for cutting tissue upon rotation of said catheter in a clockwise direction and a second cutting edge for cutting tissue upon rotation of said catheter in a counterclockwise direction; and an optical fiber insertable through said lumen of said catheter for viewing said blade; and a means for selectively heating said blade to electrocauterize tissue in said passageway.

3. A device for removing ingrown tissue from the fluid passageway of a drainage shunt which comprises:

a tubular catheter formed with a lumen and having a proximal end and a distal end, wherein said catheter is slidably insertable through said passageway of said drainage shunt, said catheter is characterized by a longitudinally oriented central axis, and said catheter is rotatable in said passageway of said shunt;

a blade attached to said catheter and extending from said distal end thereof for cutting ingrown tissue in said passageway, wherein said blade is curved and has a base and a tip, said tip being attached to said catheter and said tip being inclined toward the central axis of said catheter, and wherein said blade has a first cutting edge for cutting tissue upon rotation of said catheter in a clockwise direction and a second cutting edge for cutting tissue upon rotation of said catheter in a counterclockwise direction;

an optical fiber insertable through said lumen of said catheter for viewing said blade;

a means for selectively heating said blade to electrocauterize tissue in said passageway; and an irrigation channel formed in said tubular catheter for irrigating said passageway.

\* \* \* \* \*